US009245668B1

United States Patent
Vo et al.

(10) Patent No.: US 9,245,668 B1
(45) Date of Patent: Jan. 26, 2016

(54) LOW NOISE CABLE PROVIDING COMMUNICATION BETWEEN ELECTRONIC SENSOR COMPONENTS AND PATIENT MONITOR

(75) Inventors: Hung Vo, Fountain Valley, CA (US); Cristiano Dalvi, Lake Forest, CA (US)

(73) Assignee: Cercacor Laboratories, Inc., Irvine, CA (US)

( * ) Notice: Subject to any disclaimer, the term of this patent is extended or adjusted under 35 U.S.C. 154(b) by 431 days.

(21) Appl. No.: 13/536,881

(22) Filed: Jun. 28, 2012

Related U.S. Application Data

(60) Provisional application No. 61/502,740, filed on Jun. 29, 2011.

(51) Int. Cl.
*H01B 7/00* (2006.01)
*H01B 11/02* (2006.01)
*H01B 11/04* (2006.01)

(52) U.S. Cl.
CPC ............... *H01B 11/02* (2013.01); *H01B 11/04* (2013.01)

(58) Field of Classification Search
CPC .............. H01B 3/28; H01B 5/00; H01B 5/08; H01B 5/10; H01B 5/101–5/108; H01B 5/14; H01B 11/00; H01B 11/02; H01B 11/04; H01B 11/06; H01B 7/00; H01B 7/02; H01B 7/0216; H01B 7/0275; H01B 7/04; H01B 7/08; H01B 7/17; H01B 7/18; H01B 7/1855; H01B 7/28; H01B 9/00; H01B 9/04; H01B 11/1025; H01B 11/10

USPC ...... 174/110 R, 113 R, 117 F, 117 FF, 131 A, 174/113 C, 36, 102 R, 105 R, 106, 107, 108
See application file for complete search history.

(56) References Cited

U.S. PATENT DOCUMENTS

| | | | | |
|---|---|---|---|---|
| 4,280,507 A | * | 7/1981 | Rosenberg | 600/508 |
| 4,461,923 A | * | 7/1984 | Bogese, II | 174/36 |
| 4,960,128 A | | 10/1990 | Gordon et al. | |
| 4,964,408 A | | 10/1990 | Hink et al. | |
| 5,041,187 A | | 8/1991 | Hink et al. | |
| 5,069,213 A | | 12/1991 | Polczynski | |
| 5,163,438 A | | 11/1992 | Gordon et al. | |
| 5,319,355 A | | 6/1994 | Russek | |
| 5,337,744 A | | 8/1994 | Branigan | |

(Continued)

FOREIGN PATENT DOCUMENTS

| | | | | |
|---|---|---|---|---|
| EP | 0596344 A1 | * | 5/1993 | ........... A61B 5/0416 |
| WO | WO03/058646 A1 | * | 7/2003 | ............. H01B 11/10 |

OTHER PUBLICATIONS

US 8,845,543, 09/2014, Diab et al. (withdrawn).

*Primary Examiner* — William H Mayo, III
(74) *Attorney, Agent, or Firm* — Knobbe Martens Olson & Bear LLP

(57) ABSTRACT

A physiological measurement system can include a low noise patient cable that connects a monitor and a noninvasive optical sensor. The cable has a plurality of emitter wires configured to communicate a drive signal between the monitor and at least one emitter. The cable also has a plurality of detector wires configured to communicate a physiological signal between at least one detector responsive to the emitter and the monitor. The emitter and detector wires are orthogonally disposed so that crosstalk between the two functionally different wires is mitigated.

26 Claims, 8 Drawing Sheets

(56) References Cited

U.S. PATENT DOCUMENTS

| | | | |
|---|---|---|---|
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,483,022 A * | 1/1996 | Mar .......................... 174/128.1 |
| 5,490,505 A | 2/1996 | Diab et al. |
| 5,491,299 A * | 2/1996 | Naylor et al. .................. 174/36 |
| 5,494,043 A | 2/1996 | O'Sullivan et al. |
| 5,533,511 A | 7/1996 | Kaspari et al. |
| 5,534,851 A | 7/1996 | Russek |
| 5,552,565 A * | 9/1996 | Cartier et al. .............. 174/117 F |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,341 A * | 6/1998 | Laske et al. ................. 174/126.2 |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,796,044 A * | 8/1998 | Cobian et al. .................. 174/103 |
| 5,810,734 A | 9/1998 | Caro et al. |
| 5,823,950 A | 10/1998 | Diab et al. |
| 5,824,026 A * | 10/1998 | Diaz .............................. 607/116 |
| 5,830,131 A | 11/1998 | Caro et al. |
| 5,833,618 A | 11/1998 | Caro et al. |
| 5,834,699 A * | 11/1998 | Buck et al. ................. 174/113 R |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,937,950 A * | 8/1999 | Adams et al. ................. 174/72 R |
| 5,940,182 A | 8/1999 | Lepper, Jr. et al. |
| 5,976,070 A * | 11/1999 | Ono et al. ...................... 600/110 |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,030,346 A * | 2/2000 | Buck et al. ..................... 600/459 |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,117,083 A * | 9/2000 | Buck et al. ..................... 600/459 |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,713,673 B2 * | 3/2004 | Kao ................................ 174/36 |
| 6,714,804 B2 | 3/2004 | Al-Ali et al. |
| RE38,492 E | 4/2004 | Diab et al. |
| 6,720,497 B1 * | 4/2004 | Barsne ...................... 174/102 R |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |

(56) References Cited

U.S. PATENT DOCUMENTS

| | | | |
|---|---|---|---|
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,351,912 B2 * | 4/2008 | Lund et al. ............ 174/110 R |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty et al. |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 * | 4/2011 | Al-Ali et al. ............ 174/113 R |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |

(56) References Cited

U.S. PATENT DOCUMENTS

| | | | |
|---|---|---|---|
| 8,128,572 | B2 | 3/2012 | Diab et al. |
| 8,130,105 | B2 | 3/2012 | Al-Ali et al. |
| 8,145,287 | B2 | 3/2012 | Diab et al. |
| 8,150,487 | B2 | 4/2012 | Diab et al. |
| 8,175,672 | B2 | 5/2012 | Parker |
| 8,180,420 | B2 | 5/2012 | Diab et al. |
| 8,182,443 | B1 | 5/2012 | Kiani |
| 8,185,180 | B2 | 5/2012 | Diab et al. |
| 8,190,223 | B2 | 5/2012 | Al-Ali et al. |
| 8,190,227 | B2 | 5/2012 | Diab et al. |
| 8,203,438 | B2 | 6/2012 | Kiani et al. |
| 8,203,704 | B2 | 6/2012 | Merritt et al. |
| 8,204,566 | B2 | 6/2012 | Schurman et al. |
| 8,219,172 | B2 | 7/2012 | Schurman et al. |
| 8,224,411 | B2 | 7/2012 | Al-Ali et al. |
| 8,228,181 | B2 | 7/2012 | Al-Ali |
| 8,229,533 | B2 | 7/2012 | Diab et al. |
| 8,233,955 | B2 | 7/2012 | Al-Ali et al. |
| 8,244,325 | B2 | 8/2012 | Al-Ali et al. |
| 8,255,026 | B1 | 8/2012 | Al-Ali |
| 8,255,027 | B2 | 8/2012 | Al-Ali et al. |
| 8,255,028 | B2 | 8/2012 | Al-Ali et al. |
| 8,260,577 | B2 | 9/2012 | Weber et al. |
| 8,265,723 | B1 | 9/2012 | McHale et al. |
| 8,274,360 | B2 | 9/2012 | Sampath et al. |
| 8,301,217 | B2 | 10/2012 | Al-Ali et al. |
| 8,306,596 | B2 | 11/2012 | Schurman et al. |
| 8,310,336 | B2 | 11/2012 | Muhsin et al. |
| 8,315,683 | B2 | 11/2012 | Al-Ali et al. |
| RE43,860 | E | 12/2012 | Parker |
| 8,337,403 | B2 | 12/2012 | Al-Ali et al. |
| 8,346,330 | B2 | 1/2013 | Lamego |
| 8,353,842 | B2 | 1/2013 | Al-Ali et al. |
| 8,355,766 | B2 | 1/2013 | MacNeish, III et al. |
| 8,359,080 | B2 | 1/2013 | Diab et al. |
| 8,364,223 | B2 | 1/2013 | Al-Ali et al. |
| 8,364,226 | B2 | 1/2013 | Diab et al. |
| 8,374,665 | B2 | 2/2013 | Lamego |
| 8,385,995 | B2 | 2/2013 | Al-ali et al. |
| 8,385,996 | B2 | 2/2013 | Smith et al. |
| 8,388,353 | B2 | 3/2013 | Kiani et al. |
| 8,399,822 | B2 | 3/2013 | Al-Ali |
| 8,401,602 | B2 | 3/2013 | Kiani |
| 8,405,608 | B2 | 3/2013 | Al-Ali et al. |
| 8,414,499 | B2 | 4/2013 | Al-Ali et al. |
| 8,418,524 | B2 | 4/2013 | Al-Ali |
| 8,423,106 | B2 | 4/2013 | Lamego et al. |
| 8,428,967 | B2 | 4/2013 | Olsen et al. |
| 8,430,817 | B1 | 4/2013 | Al-Ali et al. |
| 8,437,825 | B2 | 5/2013 | Dalvi et al. |
| 8,455,290 | B2 | 6/2013 | Siskavich |
| 8,457,703 | B2 | 6/2013 | Al-Ali |
| 8,457,707 | B2 | 6/2013 | Kiani |
| 8,463,349 | B2 | 6/2013 | Diab et al. |
| 8,466,286 | B2 | 6/2013 | Bellot et al. |
| 8,471,713 | B2 | 6/2013 | Poeze et al. |
| 8,473,020 | B2 | 6/2013 | Kiani et al. |
| 8,483,787 | B2 | 7/2013 | Al-Ali et al. |
| 8,489,364 | B2 | 7/2013 | Weber et al. |
| 8,498,684 | B2 | 7/2013 | Weber et al. |
| 8,504,128 | B2 | 8/2013 | Blank et al. |
| 8,509,867 | B2 | 8/2013 | Workman et al. |
| 8,515,509 | B2 | 8/2013 | Bruinsma et al. |
| 8,523,781 | B2 | 9/2013 | Al-Ali |
| 8,529,301 | B2 | 9/2013 | Al-Ali et al. |
| 8,532,727 | B2 | 9/2013 | Ali et al. |
| 8,532,728 | B2 | 9/2013 | Diab et al. |
| D692,145 | S | 10/2013 | Al-Ali et al. |
| 8,547,209 | B2 | 10/2013 | Kiani et al. |
| 8,548,548 | B2 | 10/2013 | Al-Ali |
| 8,548,549 | B2 | 10/2013 | Schurman et al. |
| 8,548,550 | B2 | 10/2013 | Al-Ali et al. |
| 8,560,032 | B2 | 10/2013 | Al-Ali et al. |
| 8,560,034 | B1 | 10/2013 | Diab et al. |
| 8,570,167 | B2 | 10/2013 | Al-Ali |
| 8,570,503 | B2 | 10/2013 | Vo et al. |
| 8,571,617 | B2 | 10/2013 | Reichgott et al. |
| 8,571,618 | B1 | 10/2013 | Lamego et al. |
| 8,571,619 | B2 | 10/2013 | Al-Ali et al. |
| 8,577,431 | B2 | 11/2013 | Lamego et al. |
| 8,581,732 | B2 | 11/2013 | Al-Ali et al. |
| 8,584,345 | B2 | 11/2013 | Al-Ali et al. |
| 8,588,880 | B2 | 11/2013 | Abdul-Hafiz et al. |
| 8,600,467 | B2 | 12/2013 | Al-Ali et al. |
| 8,606,342 | B2 | 12/2013 | Diab |
| 8,626,255 | B2 | 1/2014 | Al-Ali et al. |
| 8,630,691 | B2 | 1/2014 | Lamego et al. |
| 8,634,889 | B2 | 1/2014 | Al-Ali et al. |
| 8,641,631 | B2 | 2/2014 | Sierra et al. |
| 8,652,060 | B2 | 2/2014 | Al-Ali |
| 8,663,107 | B2 | 3/2014 | Kiani |
| 8,666,468 | B1 | 3/2014 | Al-Ali |
| 8,667,967 | B2 | 3/2014 | Al- Ali et al. |
| 8,670,811 | B2 | 3/2014 | O'Reilly |
| 8,670,814 | B2 | 3/2014 | Diab et al. |
| 8,676,286 | B2 | 3/2014 | Weber et al. |
| 8,682,407 | B2 | 3/2014 | Al-Ali |
| RE44,823 | E | 4/2014 | Parker |
| RE44,875 | E | 4/2014 | Kiani et al. |
| 8,690,799 | B2 | 4/2014 | Telfort et al. |
| 8,700,112 | B2 | 4/2014 | Kiani |
| 8,702,627 | B2 | 4/2014 | Telfort et al. |
| 8,706,179 | B2 | 4/2014 | Parker |
| 8,712,494 | B1 | 4/2014 | MacNeish, III et al. |
| 8,715,206 | B2 | 5/2014 | Telfort et al. |
| 8,718,735 | B2 | 5/2014 | Lamego et al. |
| 8,718,737 | B2 | 5/2014 | Diab et al. |
| 8,718,738 | B2 | 5/2014 | Blank et al. |
| 8,720,249 | B2 | 5/2014 | Al-Ali |
| 8,721,541 | B2 | 5/2014 | Al-Ali et al. |
| 8,721,542 | B2 | 5/2014 | Al-Ali et al. |
| 8,723,677 | B1 | 5/2014 | Kiani |
| 8,740,792 | B1 | 6/2014 | Kiani et al. |
| 8,754,776 | B2 | 6/2014 | Poeze et al. |
| 8,755,535 | B2 | 6/2014 | Telfort et al. |
| 8,755,856 | B2 | 6/2014 | Diab et al. |
| 8,755,872 | B1 | 6/2014 | Marinow |
| 8,761,850 | B2 | 6/2014 | Lamego |
| 8,764,671 | B2 | 7/2014 | Kiani |
| 8,768,423 | B2 | 7/2014 | Shakespeare et al. |
| 8,771,204 | B2 | 7/2014 | Telfort et al. |
| 8,777,634 | B2 | 7/2014 | Kiani et al. |
| 8,781,543 | B2 | 7/2014 | Diab et al. |
| 8,781,544 | B2 | 7/2014 | Al-Ali et al. |
| 8,781,549 | B2 | 7/2014 | Al-Ali et al. |
| 8,788,003 | B2 | 7/2014 | Schurman et al. |
| 8,790,268 | B2 | 7/2014 | Al-Ali |
| 8,801,613 | B2 | 8/2014 | Al-Ali et al. |
| 8,821,397 | B2 | 9/2014 | Al-Ali et al. |
| 8,821,415 | B2 | 9/2014 | Al-Ali et al. |
| 8,830,449 | B1 | 9/2014 | Lamego et al. |
| 8,831,700 | B2 | 9/2014 | Schurman et al. |
| 8,840,549 | B2 | 9/2014 | Al-Ali et al. |
| 8,847,740 | B2 | 9/2014 | Kiani et al. |
| 8,849,365 | B2 | 9/2014 | Smith et al. |
| 8,852,094 | B2 | 10/2014 | Al-Ali et al. |
| 8,852,994 | B2 | 10/2014 | Wojtczuk et al. |
| 8,868,147 | B2 | 10/2014 | Stippick et al. |
| 8,868,150 | B2 | 10/2014 | Al-Ali et al. |
| 8,870,792 | B2 | 10/2014 | Al-Ali et al. |
| 8,886,271 | B2 | 11/2014 | Kiani et al. |
| 8,888,539 | B2 | 11/2014 | Al-Ali et al. |
| 8,888,708 | B2 | 11/2014 | Diab et al. |
| 8,892,180 | B2 | 11/2014 | Weber et al. |
| 8,897,847 | B2 | 11/2014 | Al-Ali |
| 8,909,310 | B2 | 12/2014 | Lamego et al. |
| 8,911,377 | B2 | 12/2014 | Al-Ali |
| 8,912,909 | B2 | 12/2014 | Al-Ali et al. |
| 8,920,317 | B2 | 12/2014 | Al-Ali et al. |
| 8,921,699 | B2 | 12/2014 | Al-Ali et al. |
| 8,922,382 | B2 | 12/2014 | Al-Ali et al. |
| 8,929,964 | B2 | 1/2015 | Al-Ali et al. |
| 8,942,777 | B2 | 1/2015 | Diab et al. |
| 8,948,834 | B2 | 2/2015 | Diab et al. |

(56) References Cited

U.S. PATENT DOCUMENTS

| | | |
|---|---|---|
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,084,569 B2 | 7/2015 | Weber et al. |
| 2002/0068965 A1* | 6/2002 | Sass .................... 607/122 |
| 2003/0056971 A1* | 3/2003 | Wechsler ................ 174/113 R |
| 2003/0212312 A1* | 11/2003 | Coffin et al. .............. 600/300 |
| 2005/0061536 A1* | 3/2005 | Proulx .................... 174/102 R |
| 2008/0255435 A1* | 10/2008 | Al-Ali et al. .............. 600/323 |
| 2009/0247984 A1 | 10/2009 | Lamego et al. |
| 2009/0275844 A1 | 11/2009 | Al-Ali |
| 2009/0299157 A1 | 12/2009 | Telfort et al. |
| 2010/0004518 A1 | 1/2010 | Vo et al. |
| 2010/0030040 A1 | 2/2010 | Poeze et al. |
| 2010/0261979 A1 | 10/2010 | Kiani |
| 2011/0001605 A1 | 1/2011 | Kiani et al. |
| 2011/0082711 A1 | 4/2011 | Poeze et al. |
| 2011/0105854 A1 | 5/2011 | Kiani et al. |
| 2011/0174517 A1* | 7/2011 | Al-Ali et al. .............. 174/113 R |
| 2011/0208015 A1 | 8/2011 | Welch et al. |
| 2011/0209915 A1 | 9/2011 | Telfort et al. |
| 2011/0213212 A1 | 9/2011 | Al-Ali |
| 2011/0230733 A1 | 9/2011 | Al-Ali |
| 2011/0237911 A1 | 9/2011 | Lamego et al. |
| 2012/0059267 A1 | 3/2012 | Lamego et al. |
| 2012/0116175 A1 | 5/2012 | Al-Ali et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0227739 A1 | 9/2012 | Kiani |
| 2012/0283524 A1 | 11/2012 | Kiani et al. |
| 2012/0286955 A1 | 11/2012 | Welch et al. |
| 2012/0296178 A1 | 11/2012 | Lamego et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0041591 A1 | 2/2013 | Lamego |
| 2013/0045685 A1 | 2/2013 | Kiani |
| 2013/0046204 A1 | 2/2013 | Lamego et al. |
| 2013/0060108 A1 | 3/2013 | Schurman et al. |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0109935 A1 | 5/2013 | Al-Ali et al. |
| 2013/0162433 A1 | 6/2013 | Muhsin et al. |
| 2013/0190581 A1 | 7/2013 | Al-Ali et al. |
| 2013/0197328 A1 | 8/2013 | Diab et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0274571 A1 | 10/2013 | Diab et al. |
| 2013/0296672 A1 | 11/2013 | O'Neil et al. |
| 2013/0317370 A1 | 11/2013 | Dalvi et al. |
| 2013/0324808 A1 | 12/2013 | Al-Ali et al. |
| 2013/0331670 A1 | 12/2013 | Kiani |
| 2013/0338461 A1 | 12/2013 | Lamego et al. |
| 2014/0012100 A1 | 1/2014 | Al-Ali et al. |
| 2014/0025306 A1 | 1/2014 | Weber et al. |
| 2014/0034353 A1 | 1/2014 | Al-Ali et al. |
| 2014/0051952 A1 | 2/2014 | Reichgott et al. |
| 2014/0051953 A1 | 2/2014 | Lamego et al. |
| 2014/0058230 A1 | 2/2014 | Abdul-Hafiz et al. |
| 2014/0066783 A1 | 3/2014 | Kiani et al. |
| 2014/0077956 A1 | 3/2014 | Sampath et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0125495 A1 | 5/2014 | Al-Ali |
| 2014/0127137 A1 | 5/2014 | Bellott et al. |
| 2014/0128696 A1 | 5/2014 | Al-Ali |
| 2014/0128699 A1 | 5/2014 | Al-Ali et al. |
| 2014/0129702 A1 | 5/2014 | Lamego et al. |
| 2014/0135588 A1 | 5/2014 | Al-Ali et al. |
| 2014/0142401 A1 | 5/2014 | Al-Ali et al. |
| 2014/0142402 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0200420 A1 | 7/2014 | Al-Ali |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0288400 A1 | 9/2014 | Diab et al. |
| 2014/0296664 A1 | 10/2014 | Bruinsma et al. |
| 2014/0303520 A1 | 10/2014 | Telfort et al. |
| 2014/0309506 A1 | 10/2014 | Lamego et al. |
| 2014/0316228 A1 | 10/2014 | Blank et al. |
| 2014/0323825 A1 | 10/2014 | Al-Ali et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2015/0018650 A1 | 1/2015 | Al-Ali et al. |

* cited by examiner

LOW NOISE CABLE PROVIDING COMMUNICATION BETWEEN ELECTRONIC SENSOR COMPONENTS AND PATIENT MONITOR

PRIORITY CLAIM

This application claims a priority benefit under 35 U.S.C. §119(e) from U.S. Provisional Patent Application Ser. No. 61/502,740, filed on Jun. 29, 2011, titled "Low Noise Patient Cable." The '740 provisional application is incorporated by reference herein in its entirety.

CROSS-REFERENCE TO RELATED APPLICATIONS

The present application is related to U.S. Publication No. 2003/0212312, filed on Dec. 19, 2002, entitled "Low Noise Patient Cable," which is hereby incorporated by reference in its entirety.

BACKGROUND OF THE DISCLOSURE

1. Field of the Disclosure

The present disclosure generally relates to patient monitoring devices and more specifically, embodiments of the present disclosure relate to cables connecting a monitor and a sensor of the patient monitoring device.

2. Description of the Related Art

Physiological measurement systems using spectroscopic analysis are a widely accepted noninvasive procedure for measuring patient characteristics such as oxygen and glucose levels. Measuring these characteristics is important for patient wellness because for instance, an insufficient supply of oxygen can result in brain damage and death in a matter of minutes. Thus, early detection of low blood oxygen level is of crucial importance in the medical field, especially in critical care and surgical applications. Patient monitors commercially available from Masimo Corporation of Irvine Calif., USA, measure many physiological parameters including oxygen saturation, pulse rate, perfusion, carboxyhemoglobin, methemoglobin, total hemoglobin, glucose, overall wellness, respiration, combinations of the same and others.

As shown in FIGS. 1A and 1B, a physiological measurement system consists of a monitor 101, a noninvasive optical sensor 115 applied to a patient, and a cable 111 connecting the sensor and the monitor. The system is controlled using input keys. The monitor 101 may be a portable standalone device or may be incorporated as a module or built-in portion of a multiparameter patient monitoring system. The monitor displays measurements of various physiological patient characteristics on a display 105, which may include an oxygen saturation level, a pulse rate, and an audible indication of each pulse via a speaker 107. In addition, the monitor 101 may display the patient's plethysmograph, which is a visual display of the patient's pulse contour and pulse rate, as well as a myriad of other measurements and calculated parameters.

To perform the above functions, the monitor 101 energizes one or more emitters in the sensor 115 that irradiate tissue under observation, such as, for example, a finger, toe, foot, hand, ear, forehead or the like. The radiation from the emitters is scattered and absorbed by the tissue such that some attenuated amount emerges and is detected through one or more detectors located in the sensor 115. The detector(s) produces one or more signal(s) indicative of the intensity of the detected attenuated radiation and forward the signal(s) to the patient monitor 101 for processing. The sensor 115 that houses the emitters and the detectors can be disposable, reusable, or partially reusable and disposable. Reusable sensor may include a clothespin-shaped housing that includes a contoured bed conforming generally to the shape of a finger. The emitter and detector signals are transmitted over the cable 111 connecting the monitor and the sensor.

Depending on the nature of cables and the signals that are transmitted through cables, cables can be affected by a phenomenon known as crosstalk. Crosstalk occurs when energy from one signal interferes with another signal. Such interference can cause significant distortion in the transmission of information which can lead to incorrect measurements in physiological monitoring applications. As the cable 111 often communicates high voltage emitter driving signals and low voltage sensitive detector signals, the cable 111 may unfortunately cause unwanted interference on the sensitive detector signals used to determine measurements of the physiological parameters.

SUMMARY OF THE DISCLOSURE

The present disclosure provides a low noise tinsel cable arrangement particularly suited for transmitting communications between devices. In an embodiment, the cable is used to transmit electrical signals between a physiological sensor and a physiological monitor.

In an embodiment, the cable has one or more emitter wires configured to communicate drive signals between a monitor and at least one emitter. The cable also has one or more detector wires configured to communicate a physiological signals between at least one detector and the monitor. The emitter wires transmit relatively high energy drive signals, while the detector wires transmit lower energy physiological signals. Due to the effect of crosstalk, the high energy drive/emitter signals can distort the lower energy physiological/detector signals.

This is especially problematic because, unlike the known emitter drive signals generated by the monitor, the lower energy detector signal is an unknown signal. The unknown detector signal carries the important physiological patient information, such as, for example, signals responsive to absorption signals from the detector. Often, such absorption signals are lower energy signals and thus, often are more easily distorted. Thus, reducing interference with the detector signals improves system accuracy and reliability.

Existing solutions to reduce crosstalk on the detector signals include use of different twist rates and heavy shielding in a cable. Different twist rates of wire pairs do not fully mitigate crosstalk because at certain points in the cable, the electromagnetic forces of the signals may still interact to cause interference. While a heavy shield between the wires could potentially reduce the majority of the crosstalk, this makes the cable stiff and thick. A bulky, cumbersome cable may pull the sensor away from an ideal position on the patient or pull it off altogether, leading to erroneous physiological patient information. Moreover, heavy shielding is also more susceptible to stress fractures from flexing of the cable, leading to a short lifespan. Thus, at least because of the foregoing, heavy shielding is at least somewhat of an impractical solution for communicating signals from a sensor to a spectroscopic analysis device.

The present disclosure describes mitigating crosstalk by twisting the emitter wires about the central axis of the cable in an opposing rotational direction relative to the detector wires. Opposing twists advantageously seeks to create an angle between the two functionally different wires that approaches 90 degrees. At such an angle, crosstalk is reduced without requiring heavy shielding. One embodiment twists the detector wires in one direction down the center of the cable. The detector wires are insulated with an inner shield. Then the emitter wires are twisted in another direction around the inner shield such that the angle between the emitter wires and the detector wires is about 90 degrees. Put in other terms, the detector wires are twisted clockwise and the emitter wires are twisted counterclockwise, or vice versa. The emitter wires are insulated with an outer shield, and a jacket is disposed over the outer shield to form the cable.

The disclosed opposing rotation of the wires mitigates crosstalk from the opposing rotation. This may be without or in addition to different twist rates or shielding. Opposing rotation in the cable structure may provide a more flexible cable, thereby not hindering sensor placement of the patient.

In an embodiment, tinsel wires are used to form the cable. Tinsel wires are relatively thin and strong. Using tinsel wires allows the cable to be lighter and more flexible than equivalent all metal wires. While thinner wire is advantageous in some respects, reducing the cable diameter also increases the resistance through the wires. In an embodiment, the tinsel wires may also transmit the high energy drive signals. In such embodiments, the increasing resistance places some limitations on how small the cable diameter can be. The present disclosure accomplishes satisfactory signal transmission while simultaneously reducing the cable diameter.

DETAILED DESCRIPTION OF THE PREFERRED EMBODIMENTS

Figure 1A:
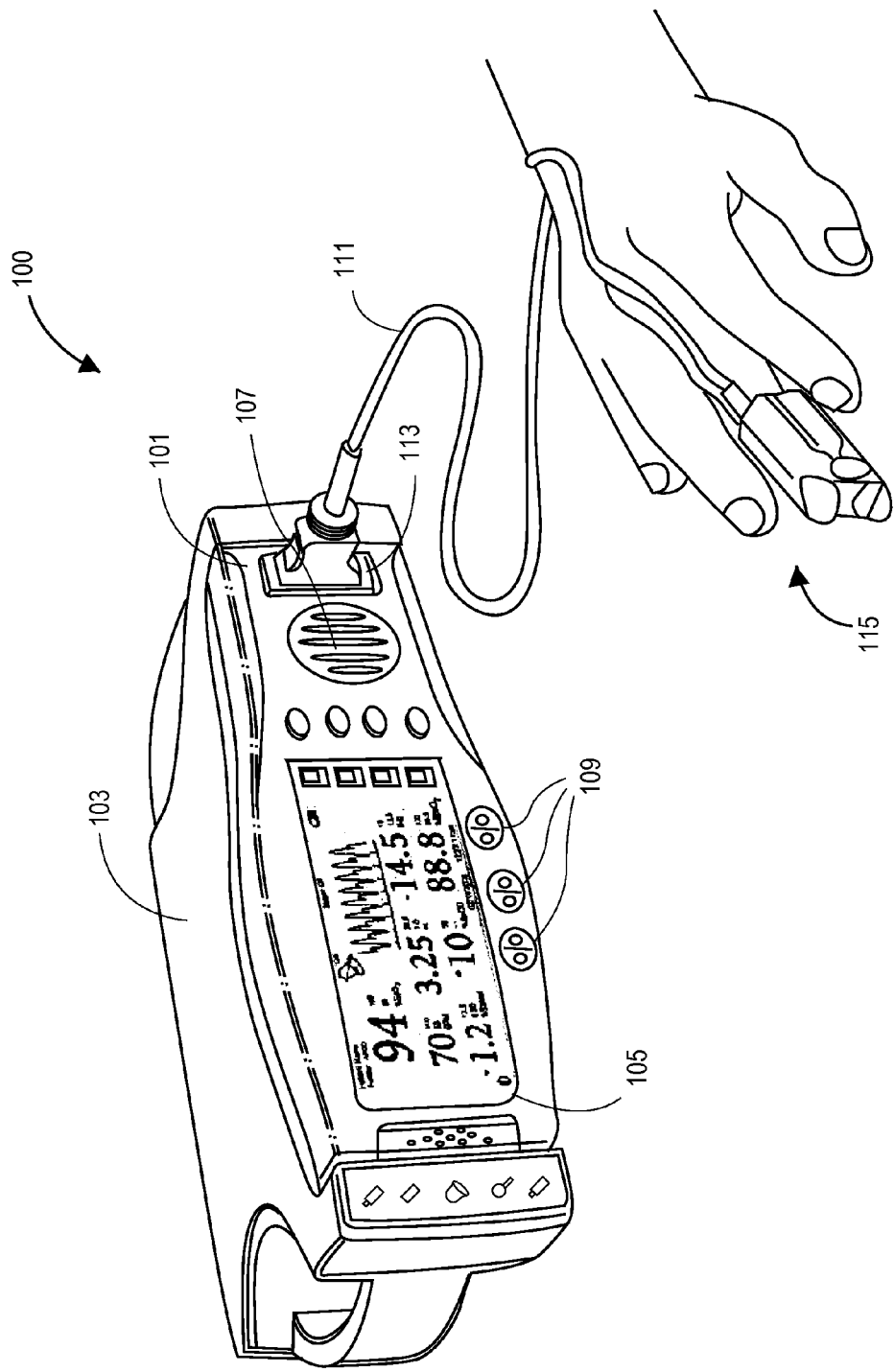
FIG. 1A illustrates a perspective view of a physiological measurement system utilizing a noninvasive optical sensor.
Figure 1B:
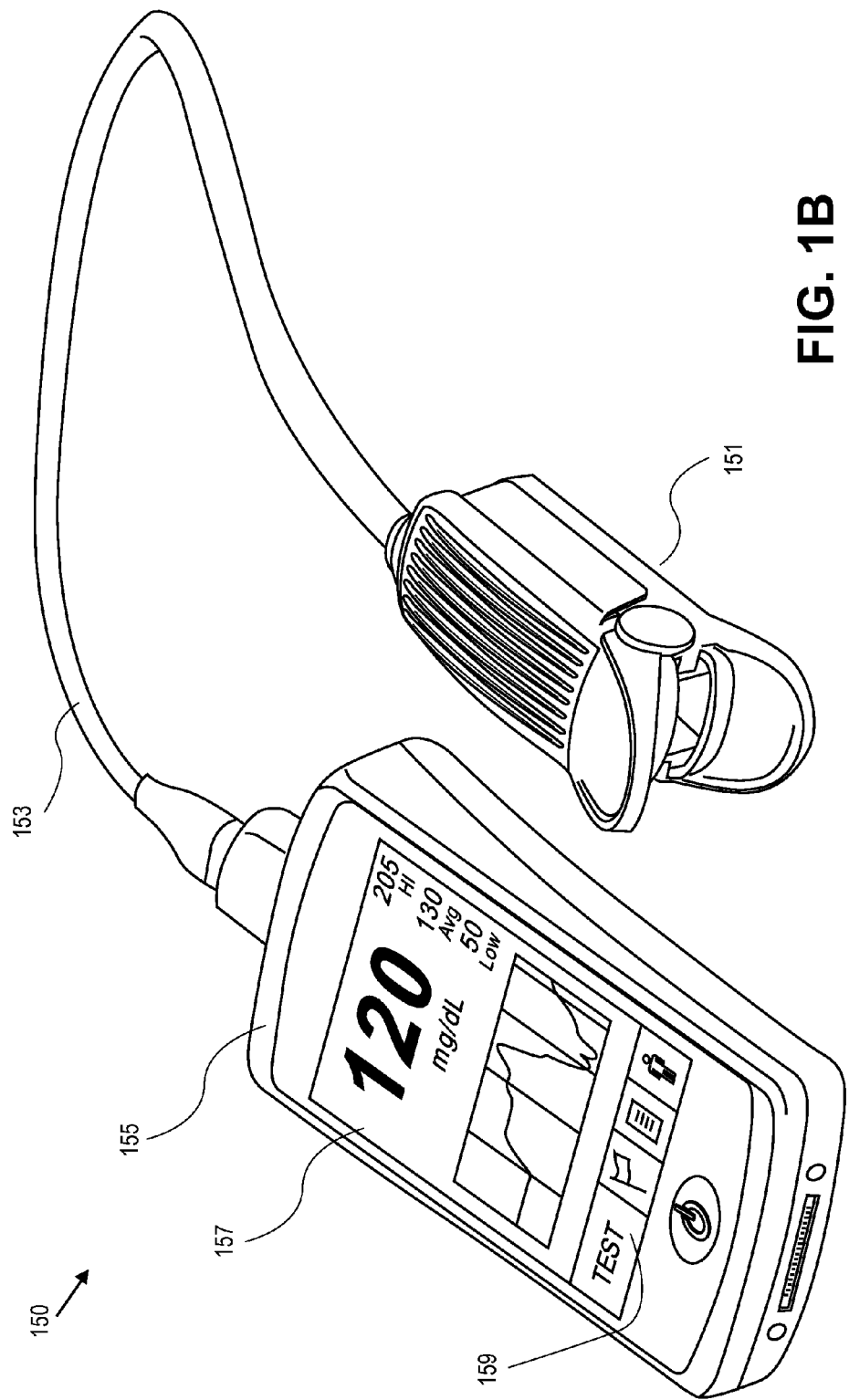
FIG. 1B illustrates a perspective view of a portable physiological measurement system utilizing a noninvasive optical sensor.

As shown in FIGS. 1A and 1B (described in more detail below), a physiological measurement systems 100 includes a monitor 101, a cable 111, and a sensor 115. The sensor 115 can be any type of physiological sensor. Illustrated in FIGS. 1A and 1B are embodiments of noninvasive optical sensors. In the case of noninvasive optical sensors, the monitor 101 sends drive signals to one or more emitters in the sensor 115 via the cable 111. The emitters irradiate tissue under observation. One or more detectors in the sensor 115 detect the radiation leaving the tissue and send a signal back to the monitor via the cable responsive to the attenuation. This sequence produces more accurate results when the noninvasive optical sensor 115 remains substantially fixed with respect to the tissue of the patient. In the embodiment where the sensor 115 comprises a reusable sensor, the sensor 115 is often held in place by only the spring action of a clothespin-shaped housing. When a cable is stiff or bulky, as a patient moves to, for example, reposition themselves, the torque from the stiff or heavy cable may be more than the tension provided by the spring, thus even slightly shifting the optical components with respect to the measurement site on the tissue. A shifted or dislodged sensor could lead to erroneous physiological patient information.

As discussed in the foregoing, a stiff or bulky cable may be the result of utilizing heavy shielding to reduce damaging crosstalk. Crosstalk occurs when the drive/emitter signals interfere with the physiological/detector signals, potentially leading to erroneous physiological patient information, similar to but for different reasons a shifted or dislodged sensor. Thus, a low noise patient cable according to the present disclosure advantageously balances reduction of stiffness and size against the competing goal of reducing crosstalk.

Various embodiments described herein disclose a cable that is relatively thin and flexible, yet is still able to mitigate crosstalk. One embodiment includes the emitter wires twisted around the detector wires such that the angle between the two functionally different wires is within a range that creates a measurable difference in crosstalk. In an embodiment, the angle is about 90 degrees. In other embodiment, the angle ranges to either side of about 90 degrees where the reduction in crosstalk is measurable and advantageous in order to accommodate other design goals, such as, for example, flexibility, shielding, etc.

By controlling the angle between the differing cables, the presently disclosed low noise cable advantageously reduces harmful crosstalk before considering additional gains that can be accomplished using different twist rates or heavy shielding.

Additionally, embodiments of the present disclosure include tinsel wires and Kevlar material. Such construction materials advantageously provide a cable structure that is relatively thin and flexible, yet strong. It is noteworthy that the Applicants recognize that use of increasingly smaller diameter cable is not necessarily the natural progression of innovation in medical cabling like the smaller is better concepts from semiconductor fabrication. In contrast to semiconductor fabrication, in patient cabling innovation, reducing the cable diameter most often increases the resistance through the thinner wires. Thus, as a cable diameter shrinks, the spectroscopic analysis devices become inoperable as signals cannot be effectively or even operably transmitted due to the increase cable properties such as resistance.

Embodiments of the low noise cable described herein balance the issues of cable diameter, resistance, shielding, etc. to disclose a cable that is thin and flexible, yet still able to effectively communicate the desired signals. This thin and flexible cable structure that mitigates crosstalk advantageously increases accuracy and reliability.

Figure 2:
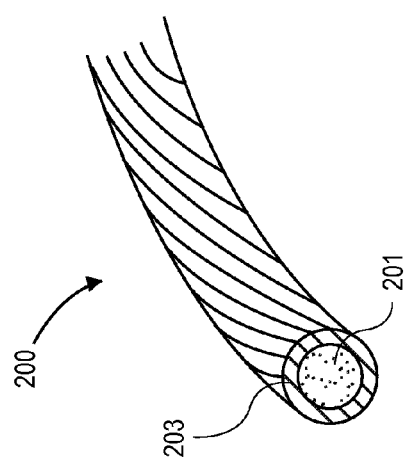
FIG. 2 illustrates a perspective view of an embodiment of an uncoated tinsel cable.

FIG. 2 illustrates a simplified perspective view of an embodiment of an uncoated tinsel cable 200. Tinsel cables as used herein include their ordinary broad meaning understood by an artisan and, from the disclosure herein, include a non-conductive fiber 201, such as, for example, aramid fiber, that is coated with a thin layer of twisted conductive material 203. In an embodiment, the conductive material 203 is a silver copper alloy. The non-conductive fiber 201 provides strength and flexibility, while the conductive material 203 allows transmission of electrical signals. The conductive layer 203 is made very thin such that flexes in the cable 200 do not cause fatigue.

Figure 3:
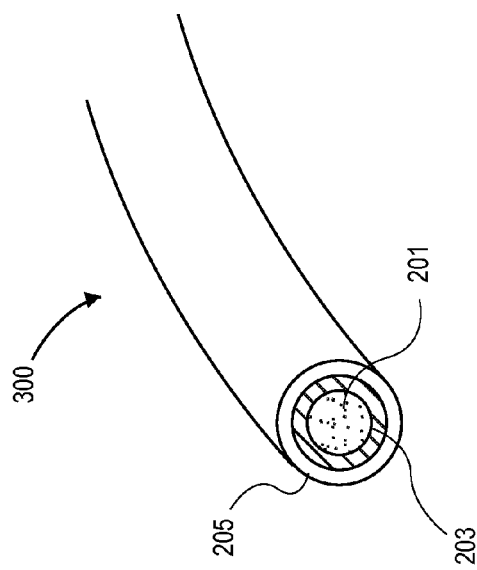
FIG. 3 illustrates a perspective view of an embodiment of a coated tinsel cable.

FIG. 3 illustrates a simplified perspective view of an embodiment of a coated tinsel cable 300. The coated cable 300 includes the same or similar materials as the uncoated tinsel cable 200, but includes a plastic outer coating 205. In an embodiment, the plastic outer coating 205 includes fluorinated ethylene propylene (FEP). An artisan will recognize from the disclosure herein that other constructions seeking to elevate associated advantages may also be used.

Figure 4:
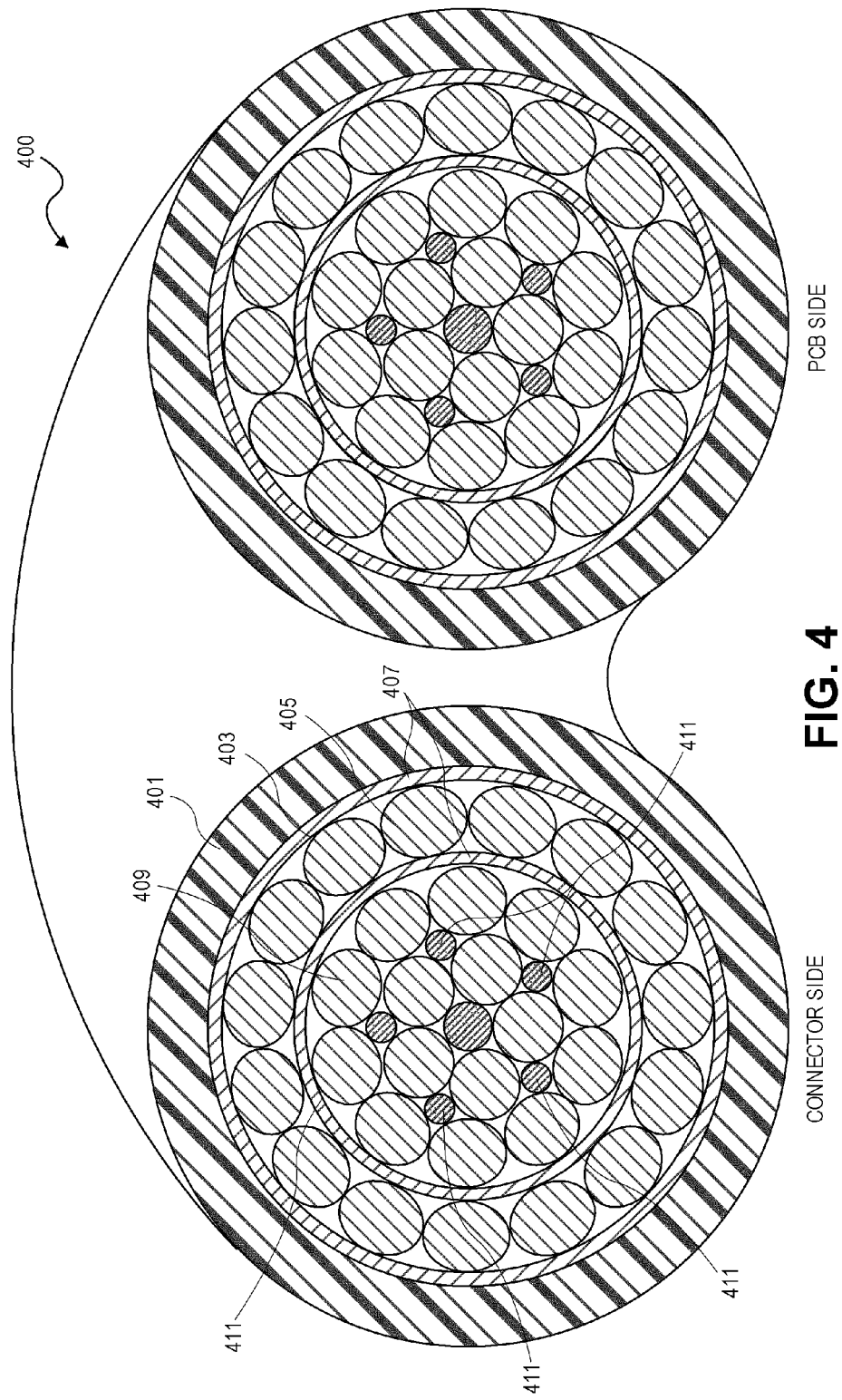
FIG. 4 illustrates a cross sectional view of an embodiment of a low noise patient cable.

FIG. 4 illustrates a simplified embodiment of a cross sectional view of each end of a low noise cable 400 according to portions of the present disclosure. The cable 400 includes an outer non-conductive protective jacket 401, an outer shield layer 403, an outer core 405, an inner shield 407, an inner core 409 and fiber filler 411. The outer non-conductive protective jacket 401 is made of flexible insulation. In an embodiment, the protective jacket 401 is UV resistant polyurethane and has a diameter of about 4.0 mm. The outer shield layer 403 is made of twisted uncoated tinsel cable. The outer core 405 is made of a single layer of twisted coated tinsel cable. The inner shield 407 is again made of twisted uncoated tinsel cable. The inner core 409 is also again made of twisted coated tinsel cable, but also includes fiber fill 411 to provide some structure to the inner core and to provide tensile strength to help prevent the cable from tearing apart. In an embodiment, the fiber fill is made of Kevlar to provide added strength. In an embodiment, the fiber fill is made of aramid fiber. In an embodiment, as illustrated in FIG. 4, the cable has six fiber fill strands 411.

In an embodiment, as illustrated in FIG. 4, there are fifteen outer core wires 405 and fifteen inner core wires 409. In other embodiments, more or fewer wires could be used depending on the application of the cable and the number of transmission paths needed. The various wires in the inner and outer cores 405 and 409 can have different colors of insulation for easy identification.

Figure 5:
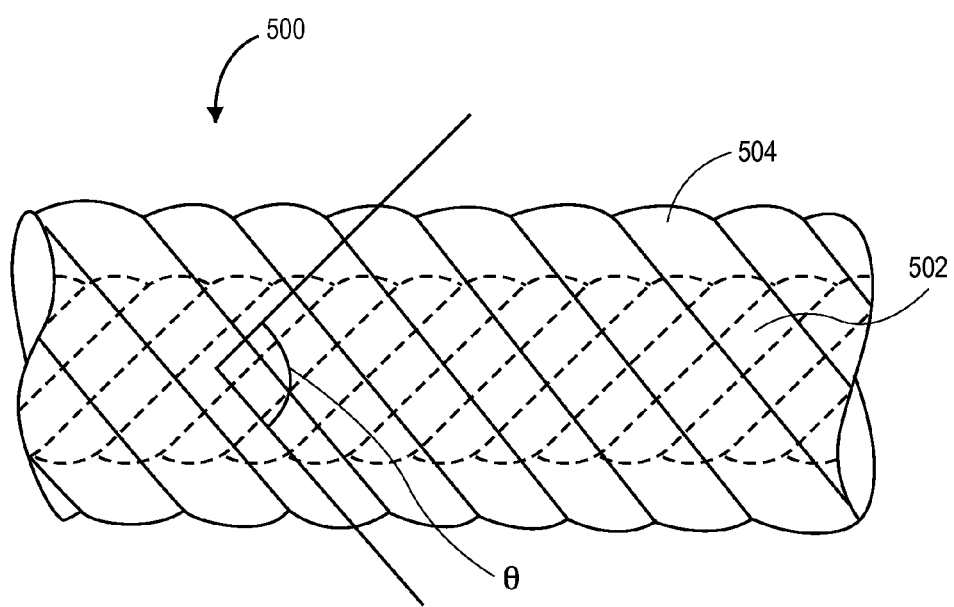
FIG. 5 illustrates a top-down view of an embodiment of the cable of FIG. 4.

In order to minimize crosstalk, the inner core 409 and the outer core 405 are twisted in opposing rotational directions. FIG. 5 illustrates the manner in which, in embodiments disclosed herein, wires in an inner core are twisted in an opposing fashion relative to wires in an outer core. FIG. 5 shows a simplified top-down view of a cable 500, which includes inner wires 502 in an inner core twisted about the central axis of the cable 500 in a helical fashion. The cable 500 also includes outer wires 504 in an outer core, which are also twisted about the central axis of the cable 500 in a helical fashion but in an opposing rotational direction from the inner wires 502. The angle θ shown in FIG. 5 indicates the angle between the outer wires 504 and the inner wires 502. Interference and crosstalk between the outer wires 504 and the inner wires 502 are reduced as the angle θ approaches 90 degrees from either direction.

For example, in one embodiment, the inner core is twisted clockwise and the outer core is twisted counter clockwise. This arrangement causes the outer core cables to be at about an angle of greater than 90 degrees to inner core cables, assisting in reducing crosstalk. In an embodiment, the angle is between about 60 and about 120 degrees. In another embodiment, the angle is between about 60 and about 90 degrees, and in a further embodiment, the angle is about 90 degrees. In still another embodiment, the angle is about 60 degrees.

In an embodiment, the inner core is used to transmit the relatively low voltage detector signals back to the monitor and the outer core is used to transmit the relatively high voltage emitter drive signals. In an embodiment, the emitter wires are the inner core wires and the detector wires are the outer core wires.

Figure 6:
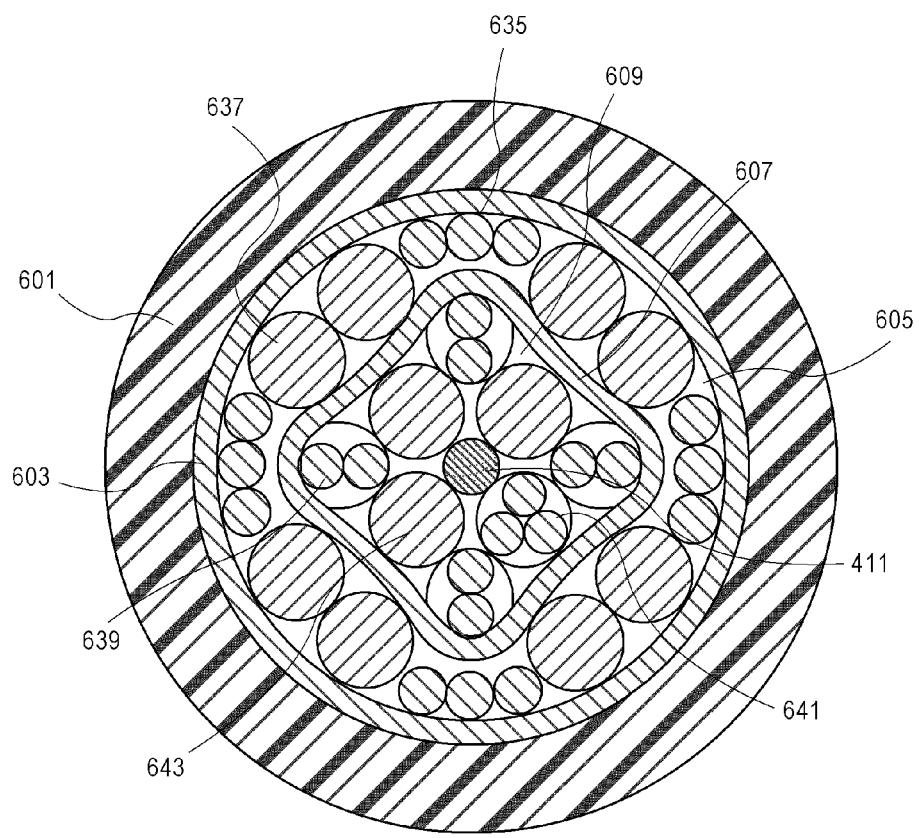
FIG. 6 illustrates a cross sectional view of an embodiment of a low noise patient cable.

FIG. 6 illustrates another embodiment of a low noise sensor cable. In this embodiment, tinsel cables are used in conjunction with standard wires, such as copper wires. In the outer core 605, there are four sets of three tinsel wires 635 and four sets of two standard wires 637 that can be any standard conducting wire such as copper. The inner core 609 includes a set of triple twisted tinsel wires 641, four sets of twisted pair tinsel wires 639 and three standard detector wires 643. As in the embodiment of FIG. 4, the inner core 609 of the FIG. 6 embodiment includes a fiber fill strand 411 to enhance the structure and tensile strength of the cable. An inner shield layer 607 separates the inner core wires from the outer core wires. An outer shield layer 603 surrounds the outer core 605. A jacket 601 is disposed over the outer shield to form the cable.

Figure 7:
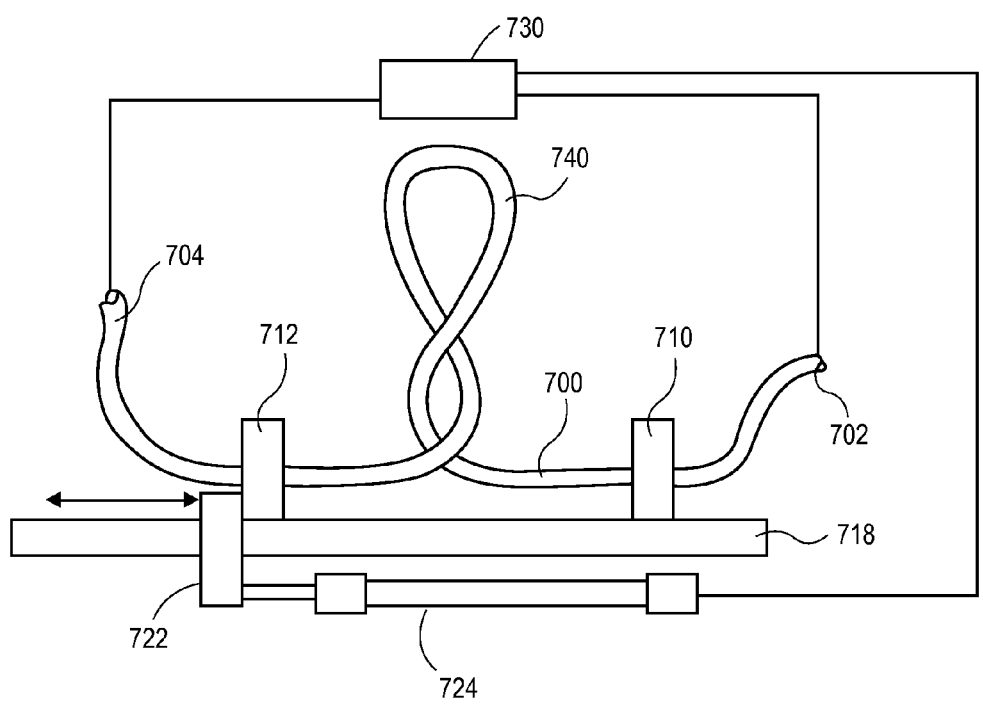
FIG. 7 illustrates a block diagram of a simplified embodiment of a kink testing apparatus for a cable.

Embodiments described herein show enhanced resilience to mechanical stresses, such as kink resistance. Cables described herein and illustrated in FIG. 4 were tested to determine their resistance to electrical failure due to mechanical breakdown of the internal conductors and/or shielding after the cable is subjected to repeated attempted kinking. FIG. 7 illustrates the test setup. The setup includes a cable 700 secured into, for example, two mounting blocks 710, 712. A section of, for example, at least about twelve (12) inches of cable 700 is used for testing. Before the cable 700 is secured to the mounting blocks 710, 712, two positions on the cable 700 approximately seven to eight inches apart are marked, and the cable 700 is grasped at those marks and twisted approximately 720 degrees. This twisting causes the cable to form a loop 740 as shown in FIG. 7, and the cable 700 is then secured to the mounting blocks 710, 712 at the marked positions.

The mounting blocks 710, 712 are attached to a track 718. The first mounting block 710 is fixed to the track 718, and the second mounting block 712 is slidably attached to the track 718. The second mounting block is also attached to a guide block 722, which is in turn driven by a pneumatic cylinder 724. The pneumatic cylinder 724 receives an air supply of approximately about 100 psi, which is regulated down to about 50 psi. This arrangement allows a tensile force of approximately 5-7 lbf. to be applied to the cable 700. When the pneumatic cylinder 724 pushes the guide block 722 and then pulls it back to the starting position, this constitutes one cycle of the test.

Figure 8:
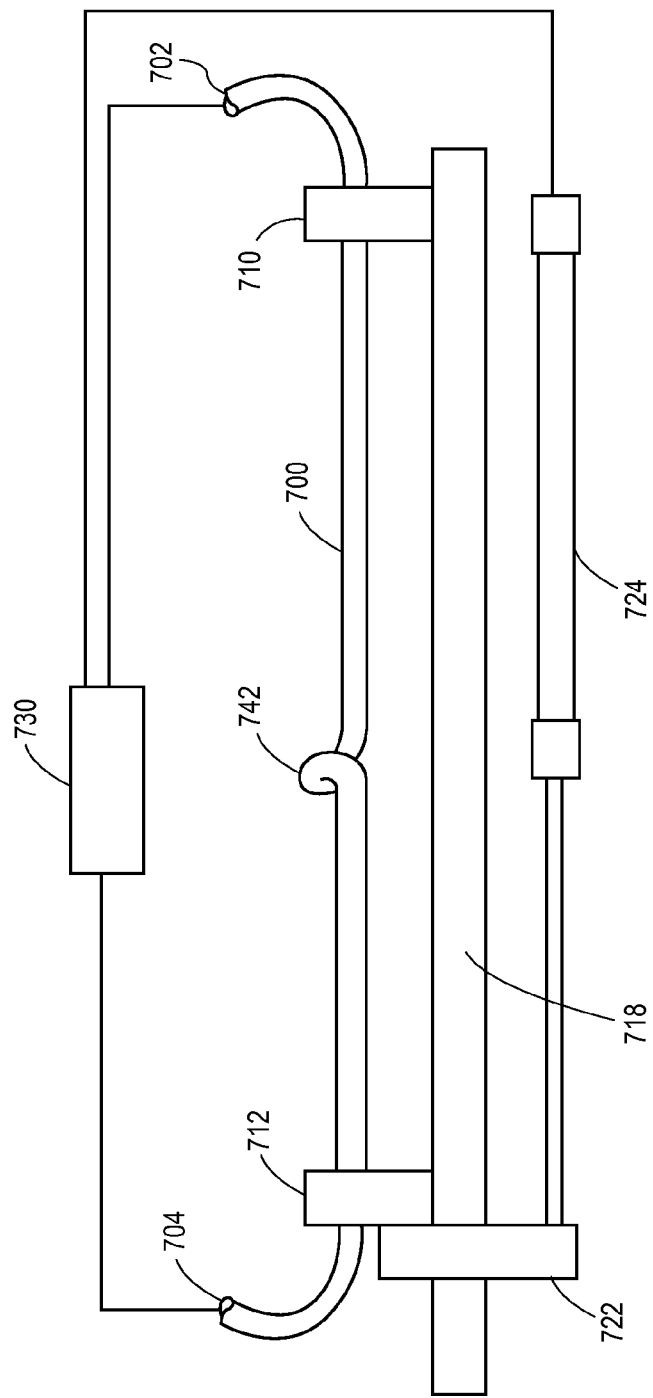
FIG. 8 illustrates the testing apparatus of FIG. 7 with the cable in a stretched position.

FIG. 7 shows the testing apparatus when the pneumatic cylinder 724 is at its starting position. Because no tensile force is being applied to the cable 700, the loop 740 is present. FIG. 8 shows the same testing apparatus when the pneumatic cylinder 724 is pushing on the guide block 722, therefore applying a tensile force to the cable 700. The effect of this tensile force is to attempt to produce a kink 742 in the cable 700.

The two ends 702, 704 of the cable 700 are electrically connected to a break detect circuit test box 730. The box 730 senses when a significant change of resistance occurs in the cable 700, and when this occurs, the box 730 sends a signal to the pneumatic cylinder 724 to stop the testing. Thus, this test repeatedly subjects the cable 700 to kinking until an electrical failure occurs. The number of cycles the cable 700 can withstand before electrical failure is an indicator of its resilience to mechanical stresses.

Twelve cable samples were subjected to this test. The results of the testing are shown below:

| Sample | Cycles to Failure |
| --- | --- |
| 1 | 13,820 |
| 2 | 6,831 |
| 3 | 12,053 |
| 4 | 9,781 |

-continued

| Sample | Cycles to Failure |
| --- | --- |
| 5 | 8,493 |
| 6 | 6,808 |
| 7 | 9,232 |
| 8 | 23,781 |
| 9 | 18,842 |
| 10 | 15,205 |
| 11 | 15,248 |
| 12 | 17,395 |

As the table shows, the smallest number of cycles producing an electrical failure for the twelve samples tested was 6,808 cycles and the largest was number of cycles was 23,781. The mean cycles-to-failure was 13,124 and the median was 12,937. These results demonstrate that the cable described herein exhibit enhanced resilience to mechanical stress. Cables described herein are capable of withstanding more than 1,500 kinks with a high degree of reliability. Reliability can be measured using a Weibull Distribution Model. Applying that model with a shape parameter of Beta=1.7, in order for the cable to reliably withstand 1,500 kinks, none of the twelve samples tested should have a failure after 6,583 kink cycles. Because the smallest number of cycles producing an electrical failure for the twelve samples tested was 6,808 cycles, the cable tested is capable of withstanding more than 1,500 kinks with a high degree of reliability. The cables described herein are capable of withstanding, on average, more than 5,000 kinks. More particularly, the cables described herein are capable of withstanding, on average, more than 10,000 kinks. Still more particularly, the cables described herein are capable of withstanding, on average, more than 12,500 kinks. In an embodiment, the cables described herein are capable of withstanding in the range or 0 to 23,000 kinks.

FIGS. 1A and 1B illustrate perspective views of physiological measurement systems utilizing a noninvasive optical sensor. Referring specifically to FIG. 1A, the physiological measurement system 100 has a portable monitor 101 and docking station 103 that houses the portable monitor 101. The portable monitor 101 has a display 105 to show physiological measurement data. The measurement data provides a readout of blood analytes, such as oxygen, carbon monoxide, methemoglobin, total hemoglobin, glucose, proteins, glucose, lipids, a percentage thereof (e.g., saturation), or other physiologically relevant patient characteristics. The portable monitor also has a speaker 107 to provide audible monitoring of physiological measurements, including, for example, the pulse rate. Utilizing control buttons, a user can operate the physiological measurement system and select between different available measurement data or other functionality for the user to manipulate, such as alarm settings, emitter settings, detector setting, and the like.

A cable 111 docks into a monitor sensor port 113 and connects to a noninvasive optical sensor 115 that is fitted on a patient utilizing a clothespin-shaped enclosure with a contoured bed conforming generally to the shape of a finger. The cable 111 can be of various lengths to allow for separation between the portable monitor 101 and sensor 115. The noninvasive optical sensor 115 has a set of emitters and detectors. The emitters serve as the source of optical radiation to irradiate patient tissue. The portable monitor 101 sends a drive signal to the emitters via the monitor sensor port 113 and through the cable 111. The emitters produce optical radiation using one or more sources of optical radiation, such as LEDs, laser diodes, incandescent bulbs with appropriate frequency-selective filters, combination of the same, or the like. The radiation from the emitters is scattered and absorbed by the tissue such that some attenuated amount emerges and is detected by one or more detectors. The detectors produce a signal indicative of the intensity of the detected attenuated radiation and forward the signal via the cable through the monitor sensor port to the portable monitor for processing.

FIG. 1B illustrates a perspective view of another portable physiological measurement system 150 utilizing a noninvasive optical sensor 151. The system of FIG. 1B is similar to that of FIG. 1A described above except that the monitor 155 is a portable standalone device instead of being incorporated as a module or built-in portion of the physiological measurement system. Moreover, the physiological measurement system 150 in FIG. 1B includes advanced functionality involving additional emitter and detectors in the sensor 151. This allows the patient physiological measurement system 150 to determine more difficult to detect parameters such as, for example, glucose and total hemoglobin. Moreover, the cable 153 is required to transmit more sensitive data that is easily corrupted by cross talk and other interference. As a result, the cabling described in the present disclosure is particularly suited to use in the patient monitor of FIG. 1B. The monitor 155 has a display 157 to show physiological measurement data and control buttons 159 that allow a user to operate the physiological measurement system 150 and select between different available measurement data or other functionality.

The term code, as used above, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

Although the foregoing invention has been described in terms of certain preferred embodiments, other embodiments will be apparent to those of ordinary skill in the art from the disclosure herein. For example, additional or alternative materials may be used to enhance the low noise cable for the known properties of the additional or alternative materials without detracting from the novelty of the present disclosure. Moreover, different or additional testing apparatuses than those of FIGS. 7 and 8 may provide useful insight into the flexibility and/or noise reduction of the present disclosure. Additionally, other combinations, omissions, substitutions and modifications will be apparent to the skilled artisan in view of the disclosure herein. Accordingly, the present disclosure is not intended to be limited by the reaction of the preferred embodiments, but is to be defined by reference to the appended claims.

Additionally, all publications, patents, and patent applications mentioned in this specification are herein incorporated by reference to the same extent as if each individual publication, patent, or patent application was specifically and individually indicated to be incorporated by reference.

What is claimed is:

1. A low noise patient cable comprising:
   a plurality of detector wires configured to communicate a physiological signal between a detector, which is responsive to energy received from an emitter, and a monitor;
   a shield disposed over the plurality of detector wires; and
   a plurality of emitter wires configured to communicate a drive signal between the monitor and at least one emitter, wherein the plurality of emitter wires are twisted in an opposing rotational direction relative to the plurality of detector wires about the shield, wherein an angle between the plurality of emitter wires and the plurality of detector wires is between about 60 degrees and about 90 degrees.

2. The low noise patient cable of claim 1, further comprising a plurality of fiber filler wires.

3. The low noise patient cable of claim 2, wherein the plurality of detector wires are tinsel wires.

4. The low noise patient cable of claim 2, wherein the plurality of fiber filler wires are Kevlar wires.

5. The low noise patient cable of claim 2, wherein the plurality of fiber filler wires are aramid wires.

6. The low noise patient cable of claim 2, further comprising a second shield disposed over the plurality of emitter wires.

7. The low noise patient cable of claim 6, further comprising a jacket disposed over the second shield.

8. A method of making a cable, the method comprising:
   twisting in a first direction a plurality of inner core wires;
   disposing a shield over the plurality of inner core wires;
   twisting in a second direction a plurality of outer core wires around the shield, the second direction being opposite the first direction; and
   disposing a jacket around the plurality of outer core wires, wherein an angle between the plurality of inner core wires and the plurality of outer core wires is between about 60 degrees and about 90 degrees.

9. The method of claim 8, further comprising twisting a plurality of fiber filler wires with the plurality of inner core wires.

10. The method of claim 8, further comprising disposing a second shield around the plurality of outer core wires.

11. The method of claim 8, further comprising twisting a plurality of fiber filler wires with the plurality of inner core wires.

12. The method of claim 11, wherein the plurality of fiber filler wires are aramid.

13. The method of claim 11, wherein the plurality of fiber filler wires are Kevlar.

14. The method of claim 8, wherein the inner and outer core wires are tinsel wires.

15. The method of claim 14, wherein the tinsel wires are made from a silver copper alloy.

16. A low noise patient cable comprising:
    a plurality of inner core wires twisted about a central axis of the cable in a first direction, the plurality of inner core wires being configured to communicate a first electrical signal;
    a shield disposed over the plurality of inner core wires;
    a plurality of outer core wires twisted about the central axis in a second direction, the second direction being opposite the first direction, wherein the plurality of outer core wires are configured to communicate a second electrical signal, wherein an angle between the second direction and the first direction is between about 60 degrees and about 90 degrees.

17. The low noise patient cable of claim 16, wherein the plurality of inner core wires are tinsel wires.

18. The low noise patient cable of claim 17, wherein the tinsel wires are a silver copper alloy.

19. The low noise patient cable of claim 16, further comprising a plurality fiber filler wires twisted with the inner core wires.

20. The low noise patient cable of claim 16, further comprising a second shield disposed over the plurality of outer core wires.

21. The low noise patient cable of claim 16, further comprising a jacket disposed over the second shield.

22. A resilient patient cable comprising:
    a plurality of detector wires configured to communicate a physiological signal between a detector and a monitor; and
    a plurality of emitter wires separated by a shield from a plurality of the detector wires, said plurality emitter wires configured to communicate a drive signal between the monitor and at least one emitter, wherein the plurality of emitter wires are twisted in an opposing rotational direction relative to the plurality of detector wires,
    wherein the cable does not electrically fail after being kinked more than 1,000 times, and wherein an angle between the plurality of emitter wires and the plurality of detector wires is about 60 degrees to about 90 degrees.

23. The resilient patient cable of claim 22, wherein the cable is capable of withstanding more than 1,500 kinks with a high degree of reliability.

24. The resilient patient cable of claim 22, wherein the cable can withstand, on average, more than 5,000 kinks before an electrical failure occurs.

25. The resilient patient cable of claim 22, wherein the cable can withstand, on average, more than 10,000 kinks before an electrical failure occurs.

26. The resilient patient cable of claim 22, wherein the cable can withstand, on average, more than 12,500 kinks before an electrical failure occurs.

* * * * *